United States Patent [19]

Rubin

[11] Patent Number: 5,005,588

[45] Date of Patent: Apr. 9, 1991

[54] METHOD FOR INCREASING TUMOR SENSITIVITY TO CHEMOTHERAPY

[76] Inventor: David Rubin, 8949 Montrose Way, San Diego, Calif. 92122

[21] Appl. No.: 421,598

[22] Filed: Oct. 13, 1989

[51] Int. Cl.[5] .............................................. A61N 1/00
[52] U.S. Cl. ..................................... 128/804; 604/20; 604/52; 514/557
[58] Field of Search .................. 128/804, 898; 600/10; 604/52, 54, 20; 424/180

[56] References Cited

U.S. PATENT DOCUMENTS

| | | | |
|---|---|---|---|
| 4,337,760 | 7/1982 | Rubin | 600/10 |
| 4,424,348 | 1/1984 | Rubin | 536/18.5 |
| 4,481,195 | 11/1984 | Rubin | 128/898 |
| 4,490,523 | 12/1984 | Rubin et al. | 536/17.1 |

OTHER PUBLICATIONS

Hurwitz, D., "Attempts at Site-Directed Experimental Chemotherapy with Antibody Drug-Conjugates," Optimization of Drug Delivery, Alfred Benzon Symposium 17. Editors: Hans Bundgaard, Anne Bagger Hansen, Helmer Kofod, Munksgaard, Copenhagen 1982.

Kartner, N. and Ling, V., "Multidrug Resistance in Cancer," Sci. Amer., Mar. 199, pp. 44–51.

Juranka et al., "P-Glycoprotein: Multidrug-resistance and a superfamily of membrane associated transport proteins," FAS, Dec. 1989 3(14) pp. 2583-2592.

Primary Examiner—Stephen C. Pellegrino
Assistant Examiner—Michael Rafa
Attorney, Agent, or Firm—Browdy & Neimark

[57] ABSTRACT

Drug-resistant tumor cells are rendered drug-sensitive by administering to the tumor cells a pump-affecting compound which suppresses the pumping action of P-glycoprotein on the tumor cells. In the case where the tumor cells have higher $\beta$-glucuronidase activity than that of the surrounding tissues, the pump-affecting compound is in the form of a $\beta$-D-glucuronide.

14 Claims, No Drawings

METHOD FOR INCREASING TUMOR SENSITIVITY TO CHEMOTHERAPY

FIELD OF THE INVENTION

The present invention relates to a method and composition for increasing the sensitivity of malignant tumors to chemotherapeutic agents.

BACKGROUND OF THE INVENTION

Chemotherapy, particularly with a combination of anti-cancer agents, is the treatment of choice for delocalized tumors that are untreatable by surgery or radiation. However, some patients relapse after even a short period of time, and do not respond to a second course of chemotherapy.

Most malignant tumors show some sensitivity to cytotoxic drugs. Accordingly, treatment with these drugs generally provides remission and shrinkage of the tumor that may last for weeks to months. Nonetheless, in many cases the tumors regrow, and this regrowth is resistant to further cytotoxic treatments.

Cancer chemotherapy has its roots in the antimicrobial chemotherapy that has been evolving since the beginning of the twentieth century. Since many microbes have now become resistant to classical antimicrobial chemotherapy, it is not surprising that clinical resistance to anticancer drugs is evident. Early experiments with tumors transplanted into mice demonstrated the development of progressive resistance to experimental drugs. Since those experiments, tumors resistant to every type of anticancer drug have been isolated. All organisms, including the cells within a malignant tumor, appear to have the ability to develop a resistance to drugs that would otherwise be fatal.

The underlying cause of progressive drug resistance, whether in infectious diseases or in cancer, is related to spontaneous genetic mutations which occur in all living cells, which mutations are inheritable and may be passed on to succeeding generations. In any cell population, mutants that are resistant to any given drug occur at a frequency of somewhere between one in $10^5$ and one in $10^8$ cells. Although this is a very rare event, it can have a large impact on the outcome of chemotherapy.

A tumor of average detectable size contains hundreds of millions of cells, some of which are likely to be drug resistant. Thus, although the mutations that produce drug resistance are quite rare, tumors containing some drug-resistant cells at the time of diagnosis may be the norm. One can easily predict the outcome of treating this type of tumor with a single drug. At first the patient will go into remission, wherein the tumor shrinks to an undetectable size because of the effects of the chemotherapy on the predominant drug-sensitive cells. However, the drug-resistant cells continue to multiply, to the point where they eventually dominate the cell population of the tumor. The tumor then grows to a size that results in the death of the patient. Experimental evidence has confirmed that even a single drug-resistant cell introduced into an otherwise curable tumor transplanted into a mouse will eventually multiply during the course of chemotherapy and dominate the tumor cell population, resulting in an incurable and ultimately fatal disease.

Theoretically it should be possible to solve this problem by administering a combination of drugs that act differently. This method of treatment is based upon the extremely small probability that two or more different drug resistances would arise spontaneously in the same cell. Combination chemotherapy appeared to obviate the problem of drug-resistant tumor cells.

Research was then directed to protocols for administering anticancer drugs in combinations. Newly developed drugs and combination chemotherapy several decades ago produced high cure rates for some childhood leukemias and for Hodgkin's disease. However, the major killers, such as lung cancer, breast cancer, and cancers of the gastrointestinal tract, remained resistant to chemotherapy.

The failures of combination chemotherapy were not understandable. Many theories were proposed to explain the observations, but few of these theories could be adequately tested. Early in the development of experimental chemotherapy in mice, simultaneous resistance of a number of drugs was an unexpectedly common occurrence. However, research focused on resistance to single agents, which at the time was more readily understood. In the late 1960's investigators experimented with drug-resistant tumor cells in vitro, and at that time the issue of multiple drug resistance resurfaced and some insights were gained into what is now known as the multidrug resistance phenotype.

These observations defined the properties of multidrug resistance. Although drug-resistant mutants were selected by means of a single anticancer drug, the cells were often simultaneously resistant (cross-resistant) to completely unrelated drugs. Most important was an observation arising from a number of independent genetic experiments: multidrug resistance appeared to result from a single mutation, i.e., a single gene could account for the multiple cross-resistance to unrelated drugs.

This observation spurred research to find the multi-drug-resistance gene in experimental tumors, stimulated inquiry into the gene's effect, and provided a rational explanation for the failures of combination chemotherapy. Since a single drug-resistant mutation is a rare event, the acquisition of multiple mutations in the same cell, yielding resistance to unrelated drugs, is an occurrence that is hugely improbable. The multidrug resistance phenotype that resulted from a single mutation explained how resistance to combination chemotherapy could be a common occurrence.

Working with various systems, investigators found that cells that were resistant to a drug somehow excluded the drug. There thus appeared to be some barrier that kept the drug from reaching the interior of the cell, where it would have its lethal effect. Two theories were provided to account for the evidence.

One theory proposed that a permeability barrier prevented drug entry into the cells. The other theory suggested that an efflux pump, a mechanism that actively pumped drug out of the cell once it had gotten inside, was at work in the resistant cells.

The latter model was based on the observations of the kinetics of drug flow into and out of the cells. It wa found that when a resistant cell was temporarily poisoned with cyanide to inhibit energy production, the cell behaved like a drug-sensitive one; it could not keep out the drug. When the cyanide was washed out and normal metabolism was restored, the cell could once again exclude the drug. Furthermore, the cell was then able to pump out the drug that had accumulated while it was poisoned. Thus, an energy-dependent drug-efflux pump seemed to be the simplest explanation.

Kartner et al., as reported in *Scientific American*, Mar., 1989, pp. 44-51, describe studies of Chinese hamster cells that were resistant to the drug colchicine. Components of the plasma membranes of the cells were separated by gel electrophoresis. This process revealed that there was a unique glycoprotein in the drug-resistant cells that appeared to be absent in the drug-sensitive cells. Glycoproteins are complex molecules made up of protein and carbohydrate, which are usually associated with the plasma membrane. The glycoprotein found associated with the Chinese hamster cells was rather large, having a molecular weight of approximately 170,000, and it was associated specifically with the plasma membrane. The glycoprotein was named P-glycoprotein for its association with the apparent permeability barrier to drugs that accompanied multidrug resistance.

A number of different groups reported similar findings with different tissue-culture systems. A variety of mouse, hamster, and human cells were selected for resistance to any one of a variety of known effective anticancer drugs: adriamycin, colchicine, daunomycin, vinblastine, vincristine, etc. All of these systems showed extensive cross-resistance to unrelated drugs, reduced intracellular accumulation of the drug involved, and alterations in the cell's surface membrane. The most consistent of the observed alterations was the appearance of a high-molecular-weight cell-surface glycoprotein similar in size to the P-glycoprotein.

It was later found that P-glycoprotein was a conserved molecule, i.e., a molecule that retains its structural identity across different mammalian species. Moreover, regardless of the species of origin or the drug of selection, the drug-resistant cells all exhibit a large elevation of P-glycoprotein expression in concert with the development of drug resistance.

Amino acid sequence studies and comparisons with other proteins led to a proposed model for P-glycoprotein structure which suggests possible ways that the protein provides multidrug resistance. It is likely that the 12 transmembrane regions of P-glycoprotein converge to form a 12-sided pore. On the outside of the cell there is little exposure of protein; this is the site where the sugar chains are attached. On the inside of the cell are two large, homologous domains projecting into the cytoplasm, which bear the ATP-binding sites. The sites that accept ATP on the P-glycoprotein molecule suggest that the protein has an energy-transducing function, such as the energy-dependent extrusion of toxic drugs from the cell.

It appears likely that the P-glycoprotein pumps drugs out of the cell in one of two ways. Either it binds a variety of drugs and extrudes them directly through the membrane by way of its putative transmembrane pore, or a second molecule (a carrier protein) binds to the drug and the drug-carrier complex is extruded across the membrane. There is evidence that some drugs may bind directly to P-glycoprotein, possibly as a first step in their ultimate transport across the surface membrane.

It has been established that in ovarian carcinomas, leukemia, and a variety of sarcomas, some of the tumors contain elevated levels of P-glycoprotein, In the small number of cases in which patient follow-ups have been possible, increased amounts of P-glycoprotein have been seen in combination with increasing unresponsiveness to chemotherapy. In perhaps 10 to 20 percent of the tumors tested, there has been clear evidence of elevated levels of P-glycoprotein.

Recently it has been found that a variety of compounds inhibit the pumping mechanism of P-glycoprotein, rendering multidrug-resistant tumor cells sensitive to drugs that would otherwise be ineffective. These compounds have been referred to as "chemosensitizers." Preliminary research indicates that some of these compounds act by interfering with the binding of drugs to P-glycoprotein, which appears to be a first step in its transport out of the cell.

There have been many reports in the prior art relating to the general concept of providing direct transport of an agent which is toxic to tumor cells directly to tumors. Reference is made, for example, to Hurwitz, E., "Attempts at Site Directed Experimental Chemotherapy with Antibody Drug-Conjugates", in *Optimization of Drug Delivery*, Alfred Benzon Symposium 17, Bundgaard, H. et al, ed., Munksgaard, Copenhagen 1982, pp. 253-269, and the various papers referenced on the first page thereof. Reports relating to the direct transport of a cytotoxic agent directly to tumors having $\beta$-glucuronidase activity by conjugating the agent with glucuronic acid are discussed in detail in Rubin et al., U.S. Pat. No. 4,481,195, which patent is hereby incorporated by reference.

Rubin et al., in U.S. Pat. No. 4,481,195 and 4,337,760, disclose methods for treating hyperacidified tumors with $\beta$-glucuronides. In the methods disclosed in these patents, tumor cells are selectively treated with nitrile-containing compounds with concurrent therapy to avoid the possibility of cyanide poisoning in the rest of the body.

SUMMARY OF THE INVENTION

It is an object of the present invention to overcome the above-noted deficiencies in the prior art.

It is another object of the present invention to provide a method and composition for overcoming drug-resistance in tumor cells.

It is a further object of the present invention to enhance the effects of anticancer drugs.

According to the present invention, resistance to cytotoxic or anticancer drugs can be overcome by administering to the patient, prior to administration of an anticancer drug, an effective amount of a compound that inhibits the pumping mechanism of P-glycoprotein. These compounds interfere with the energy required to pump cytotoxic drugs out of the cancer cell, so that the chemotherapeutic agent can be delivered to the cancer cells without the cancer cells' pumping out the chemotherapeutic agent. After the pumping mechanism of the P-glycoprotein has been inactivated, a conventional cytotoxic drug is administered, which drug is then taken into the tumor cell where it remains to kill the tumor cell. As most compounds which interfere with the energy required to pump cytotoxic drugs out of the cancer cell are toxic to normal cells, it is important that such compounds be selectively delivered only to the cancer cells.

All of the processes involved in growth and metabolism of cells require an input of energy. In most cases, this energy is suppled by hydrolysis of one or both of the high-energy phosphate bonds in adenosine triphosphate. This release of energy can be used to transport molecules against a concentration gradient.

The multidrug resistance of tumor cells is due to the existence of P-glycoprotein which serves as a pump to efflux cytotoxic drugs from the cells against the gradients to the area outside the cell. This pumping mechanism depends on energy supply, and is blocked in vitro by a number of compounds, including 2,4-dinitrophenol, 2,4-dinitrocresol, and hydrogen cyanide. The preferred compounds used in the present invention block the pumping mechanism of P-glycoprotein in the cancer cells by interfering with the production of adenosine triphosphate (ATP) in the cell. Once the pumping mechanism of the P-glycoprotein is interfered with, the cytotoxic agent can be administered to the cell where it penetrates the cell membrane and is not immediately pumped out. This enables the cytotoxic drugs to remain in the tumor cells long enough to kill the cells, and thus and to overcome the cells' resistance to chemotherapy. Of course, compounds which interfere with the pumping mechanism of P-glyco-protein by other means may also be used in the present invention. The term "pump-affecting compound" will henceforth be used throughout the present specification and claims to mean any compound which interferes with the pumping mechanism of P-glyco-protein to such an extent that when other cytotoxic agents are administered to the cells under the influence of such pumpaffecting compound, they will not immediately be pumped out. The particular mechanism of affecting such pump mechanism is not critical.

The compounds which interfere with P-glycoprotein pumping are administered in doses much less than that necessary to kill cancer cells on their own, thus diminishing their own toxicity, and are used solely to inactivate the pumping mechanism of the P-glycoprotein in chemotherapeutic-resistant cells.

While any mode of delivery of such compounds directly to the tumor cells may be used, the preferred method involves the use of the high $\beta$-glucuronidase activity known to be possessed by many types of solid tumors. Thus, pump-affecting compounds, such as compounds known to block the adenosine triphosphate pumping mechanism, can be selectively delivered to such tumor cells in the form of the glucuronide conjugate thereof. As disclosed in Rubin et al., 4,337,760, the selectivity of glucuronide compounds toward tumors can be greatly increased, and the possible deconjugation of the toxic aglycones in the body can be greatly minimized, by administering to the patient, prior to or simultaneously with administration of the glucuronide, an agent which causes hyperacidification of the already acidic tumor cells, such as glucose, and an alkalinizing agent which will maintain the pH of the rest of the body at a pH of about 7.4. It is known that at a pH of 7.4 and above, $\beta$-glucuronidase activity is substantially nil. Thus, the administration of alkalinizing agents, such as bicarbonates or other basic salts, will substantially decrease and eliminate $\beta$-glucuronidase activity which naturally occurs in certain healthy tissues, such as the kidneys, spleen, and liver. This administration of alkalinizing agent will not diminish the acidity of the tumor cells themselves, however, in view of the naturally low pH of the tumor cells, the mechanism of prior hyperacidification, and the lack of substantial blood perfusion through the tumor areas, as well as other possible mechanisms. It has even been suggested in the literature, in fact, that bicarbonate will actually increase the acidity of the cancer cells, cf. Gullino, et al., J.N.C.I., 34, 6, 857–869 (1965).

Since the $\beta$-glucuronidase activity of the tumor cells is enhanced by acidification, and the $\beta$-glucuronidase activity of the rest of the body, particularly of the kidneys, will be substantially eliminated by alkalinization, the toxic aglycones will only be released at the tumor site itself due to deconjugation of the glucuronides by the action of $\beta$-glucuronidase. Without the alkalinization step, substantial amounts of toxic material may be released, for example, in the kidneys, and the toxic aglycones so released may cause substantial damage to these organs. The greater the toxicity of the aglycones, the more important is the alkalinization step.

DETAILED DESCRIPTION OF THE INVENTION

While the compounds which interfere with the pumping mechanism of the P-glycoprotein may be administered in any manner which assures selective delivery to the tumor areas, they are preferably administered in the form of glucuronide compounds, as these compounds are very selective toward tumors having high $\beta$-glucuronidase activity. The glucuronide compounds used in the present invention may be made by the proocesses disclosed in Rubin et al., U.S. Pat. No. 4,490,523, and 4,424,348, which patents are hereby incorporated by reference. Among the glucuronide compounds that can be used are mandelonitrile-$\beta$-D-glucuronic acid; p-hydroxy-mandelonitrile-$\beta$-D-glucuronic acid; methacrylonitrile-$\beta$-D-glucuronic acid; 2,4-dinitrophenol-$\beta$-D-glucuronic acid; 2,4-dinitrocresol-$\beta$-D-glucuronic acid; 4-chloro-m -cresol-$\beta$-Dglucuronic acid; 4,6-dinitro-o-cresol-$\beta$-D-glucuronic acid; p-iodophenol-$\beta$-D-glucuronic acid; and podophyllotoxin-$\beta$-D-glucuronic acid. However, any compound that affects the pumping mechanism of P-glycoprotein, and particularly any such compound which interferes with phosphorylation of ATP, and can be delivered directly to the tumor cell, can be used in the present invention, preferably as the aglycone of a $\beta$-D-glucuronic acid. Such compounds whose aglycones have greater pump-affecting activity in an acid environment than in an alkaline environment or are water-insoluble or only poorly water-soluble in an acid environment and more water-soluble in an alkaline environment are preferred. ATP-interfering aglycones which have such properties include 2,4-dinitrophenol, 4-chloro-m-cresol and podophyllotoxin.

The free acid form of the glucuronide, or a salt thereof which will ionize at the conditions of use, is the preferred form of the compounds to be used in accordance with the present invention. However, pharmaceutically acceptable esters may also be used, although in most cases it would be expected that their activity would be somewhat lower due to their relatively lower affinity to $\beta$-glucuronidase. This is particularly true with respect to aglycones which are strong electron acceptors. Accordingly, whenever the term "glucuronide compound" is used in the present specification and claims it is understood to include not only the free glucuronic acid form of the conjugate but also pharmaceutically acceptable salts and esters thereof as discussed hereinabove.

In order to render drug-resistant cells drug-sensitive, the pump-affecting compound is first administered to the cell to interfere with the pumping mechanism. When ATP-interfering compounds are used, this is accomplished by essentially asphyxiating the P-glycoprotein activity. Then a conventional cytotoxic drug is administered, which cytotoxic drug penetrates the tumor cell membrane, it is not pumped out by the inactivated P-glycoprotein.

Any conventional chemotherapeutio drug can be administered according to the present invention.

Among the conventional chemotherapeutic drugs which can be enhanced by delivery after P-glycoprotein inactivation are 5-fluorouracil, p-hydroxyanaline mustard, methotrexate, floxuridine, cytarabine, melphalane, hydroxyurea, adriamycin, thiouracil, chlorophenol, methacrylo-nitrile, fluoroacetic acid, dinitrocresol, vinblastine, vincristine, daunomycin, and dinitrophenol.

The amount of pump-affecting compound administered is that amount which is sufficient to inactivate the pumping mechanism of the tumor cells. This amount is generally in the range of about 0.001 to about 0.01 g/kg of body weight, and is generally far less than that amount of the same compound which is required to kill the tumor cells.

The selectivity of the glucuronide compounds toward tumors can be greatly increased, and the possible deconjugation of the toxic aglycones in normal parts of the body can be greatly minimized, by administering to the patient, prior to or simultaneously with administration of the glucuronide, an agent which causes hyperacidification of the already acidic tumor cells, such as glucose, and an alkalinizing agent which maintains the pH of the rest of the body at a pH of about 7.4. It is well known that at a pH of 7.4 and above, $\beta$-glucuronidase activity is substantially nil. Thus, the administration of alkalinizing agents such as bicarbonates or other basic salts substantially decreases and eliminates $\beta$-glucuronidase activity which naturally occurs in certain healthy tissues such as the kidneys, liver, and spleen.

Administration of an alkalinizing agent does not diminish the acidity of the tumor cells themselves, however, in view of the naturally low pH of the tumor cells, the mechanism of prior hyperacidification, and the lack of substantial blood perfusion through the tumor areas, as well as other possible mechanisms. Indeed, bicarbonate may actually increase the acidity of the cancer cells; see Gullino et al., supra.

Since the $\beta$-glucuronidase activity of the tumor cells is enhanced by acidification, and the $\beta$-glucuronidase activity of the rest of the body, particularly of the kidneys, is substantially eliminated by alkalinization, the toxic pump-affecting compounds will only be released at the tumor site itself due to deconjugation of the glucuronides by the action of $\beta$-glucuronidase. Without the alkalinization step, substantial amounts of pump-affecting material, which is toxic to cells, may be released, for example, in the kidneys, and the toxic compounds so released may cause substantial damage to these organs by interfering with transport of essential ions and molecules across the cell membrane. Thus, by the use of the present invention, glucuronides of compounds which interfere with the pump activity of P-glycoprotein can be used clinically with a great degree of safety. The greater the toxicity of the pump-affecting compounds to normal cells, the more important is the alkalinization step.

In order to further reduce the possibility of release of toxic pump-affecting compounds in the entero-hepatic system, a further precaution which may be taken is to sterilize the intestines by means of neomycin in order to eliminate any $\beta$-glucuronidase-producing bacterial flora in the intestine. This may be done by administering an antibiotic, such as neomycin, orally three times a day before administering the glucuronide.

Other methods for increasing the $\beta$-glucuronidase activity at the tumor cells may be used. One method of doing this is to elevate the temperature of the toxic cells at the time of treatment. This may be accomplished by elevating the temperature of the entire body, such as by use of a pyrogenic drug or by elevating the temperature solely in the area of the toxic cells, such as by microwave radiation or electrical current. Raising of the temperature increases $\beta$-glucuronidase activity, thereby increasing the efficiency of the deconjugation of the glucuronides. It is known that an elevation of temperature of 3° C. increases $\beta$-glucuronidase activity by 50%.

Known pyrogenic drugs, such as etiocholanolone, progesterone, dinitrophenol, dinitrocresol, etc. can be used to increase the temperature of the body. Since dinitrophenol and dinitrocresol are also cytotoxic and interfere with ATP production, the use of these compounds is preferred, especially when administered as the glucuronide. When these compounds are administered, when the glucuronide is deconjugated at the tumor site, the aglycone will act not only to inhibit the activity of the P-glycoprotein but also to raise the temperature directly in the region of the tumor cells, thus greatly increasing the efficiency of further deconjugation.

Local hyperthermia in the region of tumor cells is preferred to general hyperthermia because general hyperthermia also increases the $\beta$-glucuronidase activity in healthy cells. However, because of the alkalinization step, this is not a major problem. If the hyperthermia is local, then this provides an additional degree of certainty that the glucuronides will only be deconjugated at the tumor site. The application of microwave treatment directed at the tumor site is one way to achieve local hyperthermia. Because of the different electrical resistance of tumor cells, another method of achieving some degree of local hyperthermia is by administering a small electrical current through the body.

Another manner for increasing $\beta$-glucuronidase activity selectively at the site of tumor cells is by administration of estrogen to female patients or testosterone to male patients. It has been reported that these compounds induce $\beta$-glucuronidase activity in trophoblastic cells. Certain tumor cells are known to be trophoblastic, and this method would be particularly useful for those cells. The alkalinization step would prevent damage to healthy trophoblastic cells.

Another feature of the present invention resides in an additional safety feature by which healthy tissues of the body are protected against possible release of hydrogen cyanide from nitrile-containing aglycones. This feature is preferably in addition to the feature disclosed hereinabove with respect to pH adjustment. Even with such protection against deconjugation of the glucuronide at areas of the body other than tumors, concern has been expressed about possible cyanide poisoning when using nitrile-containing glucuronides. It is theorized that it is the entire nitrile-containing aglycone which exerts the toxic effect on the tumor cells, so that it is important to protect the rest of the body against possible release of hydrogen cyanide from nitrile-containing aglycones. This is accomplished in accordance with the present invention by the concurrent administration of sodium thiosulfate when glucuronides of nitrile-containing aglycones are used. It is well known that sodium thiosulfate is an antidote for cyanide poisoning. Sodium thiosulfate in the presence of the enzyme rhodanase converts hydrogen cyanide to sodium thiocyanate.

In view of the mechanism of the present invention by which the toxic pump-affecting compound is released only at the tumor site, and in further view of the fact that very small amounts of pump-affecting compounds are used in conjunction with conventional chemotherapeutic agents, it is possible to use a number of pump-affecting agents which may not ordinarily be safe for use, including methacrylonitrile β-D-glucuronic acid.

In order to have the effect of interfering with the pump activity of the P-glycoprotein of the tumor cells, the amount of pump-affecting compound need be administered only in an amount sufficient to interfere with the P-glycoprotein pumping mechanism. Once the pumping mechanism has been intercepted, the chemotherapeutic drug is then administered in a dose lethal to the tumor cells. The chemotherapeutic drug may also be administered simultaneously with the pump-affecting compounds Hyperacidification of the tumor cells is caused by a hyperglycemic condition in the patient. Therefore, any hyperglycemic agent may be used as the hyperacidification agent, as for example, glucose, fructose, galactose, lactose, or glucagon. Furthermore, it should be understood that this hyperglycemic condition may be effected in any known manner. For example, if the patient is diabetic, then the condition can be brought about by decreasing the insulin administration.

Any agent which will raise the pH of the urine to approximately 7.4 can be used as the alkalinizing agent, including sodium or potassium bicarbonate or citrate, or other basic salts or antacids. While it is preferred that these be administered intravenously, they may be administered orally.

When the term "approximately 7.4" is used in the present specification and claims, with respect to the pH level to be maintained in the rest of the body, it should be understood that a pH level slightly above or below 7.4 may be used, although not preferred. As the pH decreases from 7.4, the β-glucuronidase activity increases until the optimal pH is reached. Furthermore, below pH 7.0 the rest of the body will not be alkaline, but will be acid. Above a pH of 7.4 the danger of alkalosis increases without any substantial further decrease in β-glucuronidase activity. A pH level of 7.4 is preferred as this is physiological pH and cannot be harmful to the body, and it is known that the β-glucuronidase activity in healthy organs is substantially nil at this pH level.

Besides intravenous administration, the pump-affecting compounds may be administered by any means of parenteral administration or by direct injection at the tumor site. When the pump affecting compounds are in the form of glucuronides, they are preferably not administered orally, as it is known that β-glucuronidase is present in the digestive tract.

The maximum amount of pump-affecting compound to be administered to any given patient must be determined empirically and will differ depending upon the condition of the patient. However, the least amount of pump-affecting compound necessary to exert the intended effect should be given so as to minimize any possible side effects, even though, due to the selective method of delivery, no substantial side effects will be expected.

Tumors which can be treated by β-D-glucuronide forms of the pump-affecting compounds are those tumors which have β-glucuronidase activity or which can be induced to have β-glucuronidase activity, so that they can cleave the glucuronide compound and release the pump-affecting compound at the tumor site. Tumors which are known to have β-glucuronidase activity include solid breast tumors and their metastases, bronchogenic carcinoma and its metastases, and lymphomas. It is also known that neoplasms that do not have high β-glucuronidase activity, and therefore cannot be treated in accordance with the present invention, include leukemia. It must be understood, however, that this list is not meant to be complete, and that the prior art is aware of many other tumors that have β-glucuronidase activity. However, whether or not the art is presently aware that any given tumor has β-glucuronidase activity, this can be determined by a variety of routine diagnostic techniques as discussed, for example, in Rubin et al. U.S. Pat. No. 4,481,195.

When it is desired to induce hyperthermia to increase β-glucuronidase activity, a method should be selected by which the temperature is raised as much as possible without risking damage to healthy portions of the body, such as the eyes. An increase of about 2° C. for whole body hyperthermia, and as much as 4.5° C. for local hyperthermia is preferred. The hyperthermia should be timed to last for about an hour at the time of greatest glucuronide concentration at the tumor site. For example, when local microwave treatment is selected, this treatment should begin about one half hour after commencement of the intravenous glucuronide drip, and be continued for about one hour. The proper dosage of known pyrogens to achieve the desired degree of hyperthermia is known to those skilled in the art, and can be easily empirically determined. For example, a dosage of about 30 mg/day of dinitrophenol would be appropriate. When estrogen or testosterone are to be administered, a dosage of from 5-15 mg/kg body weight/day would provide the desired inducement of β-glucuronidase activity.

The following non-limiting examples further illustrate the practice of the present invention.

EXAMPLE 1

The patient was an 80 year old male with a terminal pancreatic tumor. There was no evidence of improvement to the combined therapy of 20 mg adriamycin, 750 mg 5-fluorouracil, 40 mg mitomiacine, and/or 750 mg strapozorine.

The patient was then treated with mandelonitrile-β-D-glucuronic acid (DMBG) for 24 hours in the form of an intravenous drip in glucose, and the same chemotherapy was administered for 40 minutes in the middle of the DMBG treatment. The total amount of DMBG administered was 2 grams.

The dosage of 2 grams total of DMBG, in the absence of the conventional chemotherapeutic agents, had absolutely no therapeutic effect. However, when the DMBG was combined with the above chemotherapeutic agents, the patient showed a dramatic therapeutic effect. The tumor shrank and the marker Ca 19-9 was reduced from 45,000 to 140.

The above demonstrates that a very low dose of a pump-affecting compound, when delivered directly to the site of a tumor, suppresses the pumping mechanism of the P-glycoprotein and causes a drug resistant cancer to cell to become drug sensitive.

EXAMPLE 2

After it has been determined that the patient has a tumor with β-glucuronidase activity by means of conventional diagnostic methods, the patient is treated with antibiotics in order to sterilize and β-glucuronidase-producing bacteria in the intestinal flora. Preferably an antibiotic, such as neomycin, is administered three times a day, beginning at least a day prior to administration of the glucuronide and continued throughout the glucuronide treatment. After the intestines have been sterilized, a dose of glucose in the form of 100 grams of honey, glucose, or other sugar is administered. Approximately one hour later, an intravenous drip is begun of a solution in distilled water containing approximately 10% glucose and 60 milli-equivalents of sodium bicarbonate. Approximately one liter is administered, assuming no contraindications, and the pH of the urine is checked to determine that it has reached a pH of approximately 7.4. This establishes that the system has become alkalinized and that it is now safe to administer the pump-affecting glucuronide, such as dinitrophenol-β-D-glucuronic acid. Over a period of twelve hours, not more than 2 mMols of glucuronide per kilogram of body weight is administered in 100 cc of 5% dextrose solution during a 5 to 10 minute period, and this administration is repeated every hour with 1/2 of this initial loading dose. This is repeated every hour for a period of twelve hours, which is sufficient to stimulate the β-glucuronidase activity of the tumor. At this point, a mixture of adriamycin and streptozorin agents is administered as a 30 minute bolus. After the bolus has been administered, the dinitrophenol-β-D-glucuronide administration is continued for another twelve hours.

Of course, the amount and duration of pump-affecting glucuronide administration is easily determined by one skilled in the art, and the amount and duration depends upon the lifetime of the chemotherapeutic agent in the patient's circulation.

It should be understood that while the ATP-interfering compounds are the preferred compounds for use in accordance with the present invention, any other pump-affecting compound which interferes with the pumping mechanism of P-glycoprotein can be used in accordance with the present invention as long as it is capable of being selectively delivered to the tumor site by whatever mechanism is chosen. For example, if the glucuronide mechanism is used, the compound must be capable of being conjugated to glucuronic acid without losing its activity upon deconjugation. Whatever compound is used, it will exert its effect only at the tumor site in view of the selective method of delivery. Because of the selective method of delivery which is used, the toxicity which the compound may otherwise have is also not critical.

While the method of delivery utilizing glucuronide conjugation and the β-glucuronidase activity of many solid tumors, as described herein, is the preferred method of selective delivery, those of ordinary skill in the art will understand that other methods of selective delivery may also be used including, for example, antibody-drug conjugates.

The administration of glucuronides, such as mandelonitrile-β-D-glucuronic acid, in quantities sufficient to treat tumors, i.e., kill the tumor cells, is known from the previous Rubin patents cited above. The present invention uses a quantity of glucuronide which is less than that quantity necessary for effective treatment of the tumor cells. Those of ordinary skill in the art aware of the previous Rubin patents would have no reason to use less than an anti-tumor effective amount of the various glucuronides.

On even date herewith, Pat. Application Ser. No. 07/421,591 was filed by the present inventor drawn to a method and composition for relieving the localized pain caused by malignant tumors by selectively administering to local tumor sites compounds which affect the nerves at the tumor site and thus relieve the pain. Such compounds are administered in quantities insufficient to cause the death of the tumor cells. The compounds need not be administered concomitantly with chemotherapeutic agents. Among the compounds taught by said application to be usable for this purpose are mandelonitrile, p-hydroxy-mandelonitrile, and methacrylonitrile. The compounds are preferably administered in the form of the glucuronic acid conjugate thereof for selective delivery to tumors having high β-glucuronidase activity. The entire contents of said copending application are hereby incorporated herein by reference. While the pump-affecting compound of the present invention must be administered concomitantly with the administration of another chemotherapeutic agent in order to obtain its effect, the nerve-affecting compound need not be administered concomitantly with another chemotherapeutic agent in order to obtain the pain relieving effect of the invention in said copending application.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method of rendering drug-resistant tumor cells drug-sensitive, comprising selectively administering only to said tumor cells a sufficient amount of a pump-affecting compound to suppress the pumping action of P-glycoprotein on said tumor cells, said amount being less than that amount necessary for such pump-affecting compound itself to kill said tumor cells.

2. The method according to claim 1 wherein cells have higher β-glucuronidase activity than that of the surrounding tissues and said pump-affecting compound is in the form of a β-D-glucuronide.

3. The method according to claim 2 wherein the tumor cells are hyperacidified and the β-D-glucuronide compound is administered to the patient, whereby the β-glucuronidase activity of the hyperacidified tumor cells causes deconjugation of the glucuronide compound at the site of the tumor cells and release of the pump-affecting compound thereat.

4. The method according to claim 3 wherein the tumor selectivity of the process is improved and the risk of deconjugation of the glucuronide compound at the site of non-tumor tissues is diminished comprising administering to the patient an alkalinizing agent in an amount sufficient to maintain the pH level of the non-tumor tissues of the patient at approximately 7.4 during the glucuronide treatment.

5. The process according to claim 4 wherein the glucuronide compound is one in which the aglycone exerts a higher pump-affecting effect in an acid environment than in an alkaline environment or is water-insoluble or only poorly water-soluble in an acid environment and more water-soluble in an alkaline environment.

6. A process according to claim 2 wherein the glucuronide compound is selected from the group consisting of 2,4-dinitrophenol-β-D-glucuronic acid; 2,4-dinitrocresol -β-D-glucuronic acid; 4-chloro-m-cresol-β-D-glucuronic acid; 4,6-dinitro-o-cresol-β-D-glucuronic acid; podophyllotoxin -β-D-glucuronic acid; p-iodophenol-β-D-glucuronic acid; mandelonitrile-β-D-glucuronic acid; 1-hydroxy-mandelonitrile -β-D-glucuronic acid and methacrylonitrile-β-D-glucuronic acid.

7. The process in accordance with claim 3 wherein said step of hyperacidifying the tumor cells comprises administering a hyperglycemic agent in an amount sufficient to hyperacidify the tumor cells.

8. A process in accordance with claim 2 wherein said alkalinizing agent is administered orally or intravenously.

9. A process in accordance with claim 4 further including the step of inducing hyperthermia at least at the site of the tumor being treated to an extent sufficient to substantially increase β-glucuronidase activity at the site without substantially affecting the overall health of the patient at least at the time of maximum glucuronide concentration at the tumor.

10. A process in accordance with claim 9 wherein said hyperthermia is induced locally at the tumor by administration of the glucuronide of a pyrogen, by microwave treatment, or by passage of electrical current through the body.

11. A process in accordance with claim 1 wherein said pump-affecting compound is one which interferes with the production of adenosine triphosphate in the tumor cells.

12. A method for the treatment of patients having tumors with β-glucuronidase activity, comprising administering to such patients a β-D-glucuronic acid conjugate of a compound having pump-affecting properties, in an amount sufficient to suppress the pumping of P-glycoprotein on said tumor cells, said amount being less than that amount necessary for said conjugate itself to kill said tumor cells, and, while the tumors are being contacted by said compound, administering an effective amount of a chemotherapeutic agent other than a β-D-glucuronic acid conjugate.

13. A method in accordance with claim 12, further including the step of, prior to administering said glucuronic acid conjugates, causing the tumors to become hyperacidified and causing the healthy tissues of the remainder of the patient to become alkalinized.

14. A method in accordance with claim 12, wherein said chemotherapeutic agent is selected from the group consisting of 5-fluorouracil, p-hydroxyanaline mustard, methotrexate, floxuridine, cytarabine, melphalan, hydroxyurea, adriamycin, thiouracil, chlorophenol, methacrylonitrile, fluoroacetic acid, melphalan, dinitrocresol, vinblastine, vincristine, daunomycin, and dinitrophenol.

* * * * *